US009943548B2

United States Patent
Rolfo et al.

(10) Patent No.: US 9,943,548 B2
(45) Date of Patent: Apr. 17, 2018

(54) PREECLAMPTIC PLACENTAL MESENCHYMAL STEM CELL CONDITIONED MEDIUM FOR USE IN THE TREATMENT OF A TUMOUR

(71) Applicant: CORION BIOTECH S.r.L., Turin (IT)

(72) Inventors: Alessandro Rolfo, Turin (IT); Tullia Todros, Turin (IT)

(73) Assignee: Corion Biotech S.R.L., Torino (IT)

( * ) Notice: Subject to any disclaimer, the term of this patent is extended or adjusted under 35 U.S.C. 154(b) by 0 days.

(21) Appl. No.: 14/432,722

(22) PCT Filed: Oct. 2, 2013

(86) PCT No.: PCT/IB2013/059064
§ 371 (c)(1),
(2) Date: Mar. 31, 2015

(87) PCT Pub. No.: WO2014/054004
PCT Pub. Date: Apr. 10, 2014

(65) Prior Publication Data
US 2015/0250823 A1 Sep. 10, 2015

(30) Foreign Application Priority Data
Oct. 2, 2012 (IT) .................. TO2012A0859

(51) Int. Cl.
A61K 35/28 (2015.01)
A61K 38/19 (2006.01)
A61K 38/20 (2006.01)
A61K 38/18 (2006.01)
A61K 38/46 (2006.01)
A61K 45/06 (2006.01)
A61K 38/45 (2006.01)

(52) U.S. Cl.
CPC .......... A61K 35/28 (2013.01); A61K 38/1866 (2013.01); A61K 38/19 (2013.01); A61K 38/191 (2013.01); A61K 38/193 (2013.01); A61K 38/195 (2013.01); A61K 38/20 (2013.01); A61K 38/204 (2013.01); A61K 38/2033 (2013.01); A61K 38/2046 (2013.01); A61K 38/2053 (2013.01); A61K 38/2066 (2013.01); A61K 38/2086 (2013.01); A61K 38/45 (2013.01); A61K 38/465 (2013.01); A61K 45/06 (2013.01); C12Y 207/10 (2013.01); C12Y 301/27008 (2013.01)

(58) Field of Classification Search
None
See application file for complete search history.

(56) References Cited
U.S. PATENT DOCUMENTS
2007/0087986 A1 4/2007 Premack et al.

FOREIGN PATENT DOCUMENTS
WO 2013093878 A1 6/2013

OTHER PUBLICATIONS

The abstract by Rolfo et al., Sep. 2011; Placenta 32 Abstract #P1.110; p. A64.*
Battula et al., Differentiation, 2007; 75: 279-291.*
Brooke et al., Br J Haematol. 2009; 144: 571-579.*
Deng-Bryant et al., Restor Neurol Neurosci. 2015; 33: 189-203.*
Tannock and Hill. The Basic Science of Oncology. 1998. New York: McGraw-Hill; p. 357.*
Song et al., Expert Opin Biol Ther 7(4): 431-438, 2007.*
Rolfo et al., Aging Male, 2014; 17: 94-101.*
Grivennikov et al., Cell, 210; 140: 883-899.*
Grivennikov et al., Cell; 140: 883-899. (Year: 2010).*
Huang, et al., "Isolation of Mesenchynal Stem Cells from Human Placental Decidua Basalis and Resistance to Hypoxia and Serum Deprivation", Stem Cell Rev and Rep, May 23, 2009, 5:247-255.
Ruster, et al., "Mesenchymal Stem Cells Display Coordinated Rolling and Adhesion Behavior on Endothelial Cells", Blood Journal, Dec. 1, 2006, vol. 108, No. 12, pp. 3938-3944.
Nevo, et al., "Placental Expression of Soluble fms-Like Tyrosine Kinase 1 is Increased in Singletons and Twin Pregnancies with Intrauterine Growth Restriction", J Clin Endocrinol Metab, Jan. 2008, 93(1):285-292.
International Search Report dated Feb. 27, 2014.
Marta Magatti et al. "Amniotic membrane-derived cells inhibit proliferation of cancer cell lines by inducing cell cycle arrest"; Journal of Cellular and Molecular Medicine; vol. 16, No. 9, Aug. 23, 2012, pp. 2208-2218.
Hwang J H et al. "Cytokine expression in placenta-derived mesenchymal stem cells in patients with pre-eclampsia and normal pregnancies"; Cytokine Academic Press Ltd, Philadelphia PA, US; vol. 49, No. 1, Jan. 1, 2010, pp. 95-101.
Y. Wang et al. "Endothelial angiotensin II generation induced by placenta-derived factors from pre-eclampsia"; Reproductive Sciences; vol. 15, No. 9, Nov. 1, 2008, pp. 932-938.
Y. Wang et al "Increased neutrophil-endothelial adhesion induced by placental factors is mediated by platelet-activating factor in preeclampsia"; Journal of the Society for Gynecologic Investigation, Elsevier, New York, NY, US; vol. 6, No. 3, May 1, 1999, pp. 136-141.
Ackerman W E et al. "IFPA Meeting 2011 workshop report III: Placental immunology; epigenetic and microRNA-dependent gene regulation; comparative placentation; trophoblast differentiation; stem cells", Placenta, W.B. Saunders, GB, vol. 33, Nov. 24, 2011, pp. S15-S22.

(Continued)

Primary Examiner — Christina M Borgeest
(74) Attorney, Agent, or Firm — Thomas | Horstemeyer LLC

(57) ABSTRACT

It is described a conditioned medium (CM) obtainable by culturing, in a liquid culture medium, placental mesenchymal stem cells from a preeclamptic placenta. The conditioned medium object of the invention includes at least IP-10 and TARC proteins and it is used for the therapeutic treatment of a tumor, preferably an epithelial tumor.

8 Claims, 2 Drawing Sheets

(56) References Cited

OTHER PUBLICATIONS

Yust-Katz Shlomit et al "Placental mesenchymal stromal cells induced into neurotrophic factor-producing cells protect neuronal cells from hypoxia and oxidative stress"; Cytotherapy Jan. 2012, vol. 14, No. 1, Oct. 31, 2011, pp. 44-45.
Alessandro, Rolfo et al. "Pro-inflammatory profile of preeclamptic placental mesenchymal stromal cells: new insights into the etiopathogenesis of preclampsia"; PLOS One; vol. 8, No. 3, Mar. 19, 2013, p. e59403.

* cited by examiner

PREECLAMPTIC PLACENTAL MESENCHYMAL STEM CELL CONDITIONED MEDIUM FOR USE IN THE TREATMENT OF A TUMOUR

CROSS-REFERENCE TO RELATED APPLICATION

This application is the 35 U.S.C. § 371 national stage of PCT Application No. PCT/IB2013/059064, filed Oct. 2, 2013, which is herein incorporated by reference in its entirety and which also claims priority to, and the benefit of, Italian Patent Application No. TO2012A000859, filed Oct. 2, 2012, which is herein incorporated by reference in its entirety.

The present invention relates to the field of therapeutic treatments for tumoral pathologies.

During the last decades, anti-tumoral therapies made important advances, thus allowing an increasing number of cases to positively modify the prognosis, once inexorably ominous, thereby making them treatable and sometimes curable. However, conventional tumor therapies are still primarily based on surgical interventions, if the tumor site and stage of the disease do allow them. Surgical interventions are usually accompanied by chemo- and/or radio-therapy treatments, unfortunately associated with severe side effects. Chemotherapy is systemically administered, therefore its cytotoxic effects could indiscriminately target both cancer and healthy cells, in particular in those tissues characterized by an high proliferation rate. Indeed, chemotherapy could cause the onset of additional pathological conditions such as myelosuppression and mucositis. Radiotherapy can also induce severe side effects caused essentially by healthy cells DNA damage during irradiation of the tumor area. This phenomenon could even lead to the formation of secondary tumors.

Therefore, clinical oncologic research focused on the assessment of alternative therapeutic approaches able to exert a more targeted action on neoplastic cells, for example through the use of therapeutic agents that selectively interfere with those cellular mechanisms specifically activated during cancer cell growth and metastatic invasion of neoplastic cells as well as during tumor neo-angiogenesis.

Among the more innovative solutions, the stem cell based therapies, including those approaches that use stem cells and factors produced by stem cell under physiological conditions, play an important role.

In particular, recent experimental evidences suggest that human embryonic stem cells are able to secrete trophic factors which can selectively inhibit in-vitro proliferation and tumorigenesis of cancer cells. Anti-tumoral activity was also reported in adult mesenchymal stem cells (MSC) isolated from bone marrow and adipose tissue. For example, it was observed in in-vivo mice models that intravenously administered human MSCs are able to selectively migrate toward the malignant tissue, to integrate in the tumoral stroma and to inhibit cancer cells proliferation. On the basis of this peculiar MSCs tropisms toward active tumorigenesis sites, additional therapeutic applications for MSCs have been recently developed. These methods involve the use of mesenchymal cells as vehicles to selectively deliver biological molecules with anti-neoplastic activity directly in the tumor area.

Despite the above mentioned promising results, the application of human stem cells in clinical practice is still a challenge. Human embryonic stem cells entail important ethical and biosafety issues because their limited characterization makes hard to predict potential side effects like the incidence of secondary tumors. On the other hand, the therapeutic use of MSC implies their harvesting from bone marrow or adipose tissue by highly invasive procedures, together with the necessity to expose these cells to difficult and expensive ex-vivo expansion methods because of their native low concentrations (0.001% of mononucleated cells in the bone marrow).

Recent studies reported the presence in the mesenchyme of placental chorionic villi and in the amniotic membranes of a particular cell population named placental mesenchymal stem cells (PDMSC) (Huang Y C, Yang Z M, Chen X H, Tan M Y, Wang J, Li X Q, et al. *Isolation of mesenchymal stem cells from human placental decidua basalis and resistance to hypoxia and serum deprivation*. Stem Cell Rev. 2009; 5(3):247-55). Due to the unique features of the placental tissue, these cells possess a stem-mesenchymal phenotype that provides them, along with an elevated proliferative and differentiation potential, with the fundamental feature of having a well defined life-span and a controlled proliferation rate, thus reducing the potential risk of secondary tumors formation associated with their in-vivo use. Moreover, PDMSCs are able to exert immunosuppressive and anti-inflammatory activities.

On the basis of the above mentioned unique plastic and differentiation properties, as well as the easiness to retrieve and use the placental tissue, placental mesenchymal stem cells have become subject of intense investigation, mainly in the field of regenerative medicine. Rüster B. and colleagues reported that MSC possess the ability to spontaneously migrate toward damaged organs and tissues to take part to the reparative process (Rüster B, Göttig S, Ludwig R J, Bistrian R, Müller S, Seifried E, et al. *Mesenchymal stem cells display coordinated rolling and adhesion behavior on endothelial cells*. Blood. 2006; 108(12):3938-44). The absence of immunogenicity typical of mesenchymal stem cells, due to lack of expression of HLA-II and co-stimulatory molecules (CD80, CD86, CD40) necessary to directly stimulate T lymphocytes and to confer lysis resistance to cytotoxic T lymphocytes, further support their application in regenerative medicine. Other studies demonstrated that PDMSCs derived from the amniotic membranes of physiological placentae can exert an inhibitory effect on tumoral cell lines proliferation (Magatti M, De Munari S, Vertua E, Parolini O. *Amniotic Membrane-Derived Cells Inhibit Proliferation of Cancer Cell Lines by Inducing Cell Cycle Arrest*. J Cell Mol Med. 2012 Jan. 19. doi: 10.1111/j.1582-4934.2012.01531.x.)

International patent application No. WO 2013/093878 discloses the use of a culture media conditioned by PDMSC cells isolated from chorionic villi of term physiological human placentae for the therapeutic treatment of preeclamptic syndrome. Preeclampsia is a severe human pregnancy-related syndrome characterized by an exacerbated maternal-placental inflammatory response, generalized endothelial damage and defective placental development.

Figure 1:
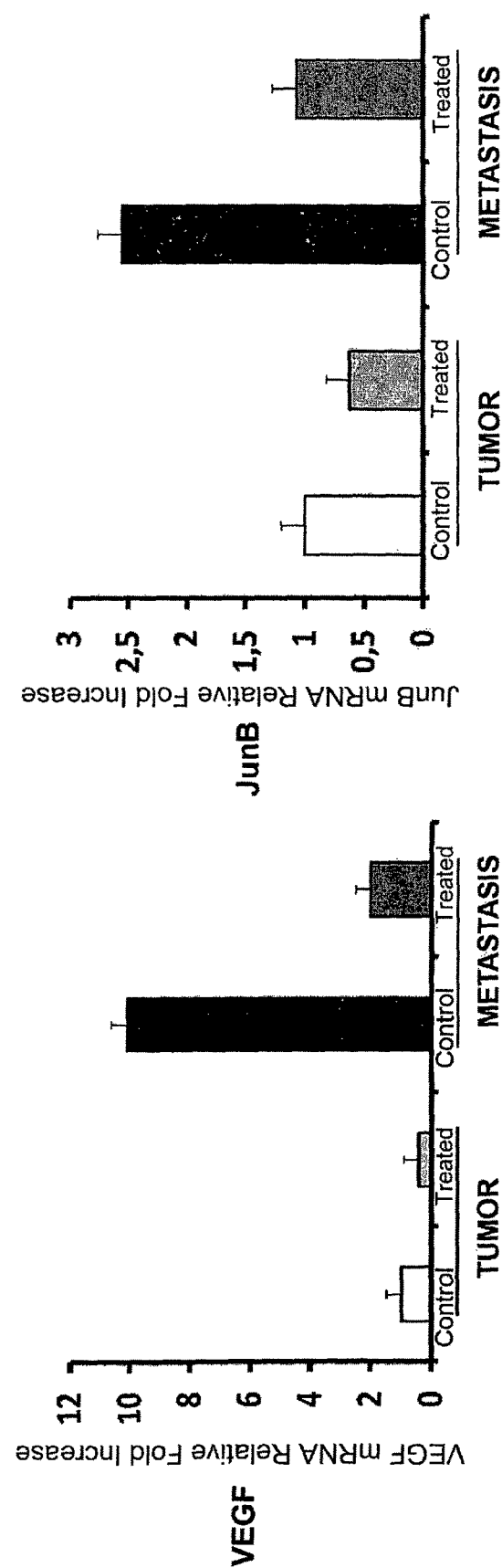
FIG. 1 shows treatment of primary and metastatic tumoral breast tissue explants by the disclosed conditioned media induces a decrease in the expression levels of VEGF ("Vascular Endothelial Growth Factor") and in the transcriptional factor JunB.

As it will be illustrated with further details in the following experimental section, the present inventors observed that conditioned medium (CM) produced by culturing in a liquid culture media placental mesenchymal stem cells isolated from human placentae affected by preeclampsia, exerts a surprising inhibitory effect on tumoral proliferation and angiogenesis. In particular, as illustrated in FIG. 1, the treatment of primary and metastatic tumoral breast tissue explants by the above mentioned conditioned media induces a significant and surprising decrease in the expression levels of VEGF ("Vascular Endothelial Growth Factor") compared to controls, well known as the main vascular growth factor involved in the tumoral neo-angiogenesis processes, and in the transcriptional factor JunB, oncogene member of the Activating Protein-1 (AP-1) family which expression is directly correlated to a bad prognosis of breast cancer. The therapeutic efficacy of these cells is really surprising, since the conditioned medium obtained by culturing physiological placental mesenchymal stem cells exerts on tumoral explants an opposite effect by stimulating vasculogenesis.

The experimentally demonstrated inhibitory effect exerted on angiogenesis processe and on tumoral cells proliferation, which turned out to be particularly effective also on cancer tissues at an advanced stage, is strongly indicative of the clinical anti-tumoral effectiveness of the conditioned medium obtainable by culturing in a liquid culture medium placental mesenchymal stem cells from human preeclamptic placentae.

The experimental approach followed by the inventors in order to identify the proteins secreted by preeclamptic PDMSCs that concertedly contributes to the CM anti-tumoral effects described above, was based on the proteomic analysis of the mentioned medium by using a commercially available antibody array able to specifically and simultaneously recognize several different cytokines, chemokines and growth factors. The results of the proteomic analysis allowed the identification of several factors, mentioned below, among which IP-10 (Interferon gamma induced protein 10) and TARC (Thymus and Activation Regulated Chemokine) are crucial.

Therefore, a subject-matter of the invention is a conditioned medium (CM) obtainable by culturing, in a serum-free liquid basal medium, a placental mesenchymal stem cell isolated from a preeclamptic placenta, and comprising at least IP-10 and TARC factors, for use in the therapeutic treatment of a tumor. Moreover, the subject-matter of the invention includes a method of producing the conditioned medium and a pharmaceutical composition that comprises IP-10 and TARC proteins, everything as defined in the attached claims that constitute an integral part of the present description.

In the present description, the term "placental mesenchymal stem cell from preeclamptic placenta" indicates a mesenchymal stem cell derived from the placenta of a pregnant woman affected by the preeclamptic syndrome. The pregnant subject is preferably a human subject.

Mesenchymal stem cells of placental origin belong to different populations, on the basis of the placental tissue of origin. Indeed, the human placenta possesses a unique structure, which includes fetal tissues, such as the chorion (chorion frondosum and smooth chorion) and the amnion, and maternal-derived tissues, such as the decidua.

In a preferred embodiment, the conditioned medium which is the subject-matter of the invention, is obtainable by culturing a placental mesenchymal stem cell of chorionic origin. Preferably, but in a non-limitative way, the chorionic mesenchymal stem cell is characterized by the surface antigens features illustrated in the following Table, that were detected by cytofluorimetric analysis.

| Marker | Cytofluorimetric Analysis |
| --- | --- |
| HLA I | + |
| CD105 (Endoglin) | + |
| CD166 (ALCAM) | + |
| CD90 (Thy-1) | + |
| CD73 (5'-nucleotidasi) | + |
| CD34 | − |
| HLA-DR | − |
| CD133 (Prominin-1) | − |
| CD20 | − |
| CD326 (EpCAM) | − |
| CD31 (PECAM-1) | − |
| CD45 (PTPRC) | − |
| CD14 | − |

Alternatively, to prepare the conditioned media, an amnion-derived mesenchymal stem cell that presents the surface antigen features illustrated in the above mentioned table is used.

The conditioned medium which is the subject-matter of the present invention, comprises at least IP-10 and TARC, secreted proteins that are renowned for their anti-tumoral activity. IP-10 chemokine, member of the CXC family, is a key mediator of the Interferon gamma (IFN gamma) anti-tumoral activity, because, after being induced by IFN gamma, IP-10 is able to attract CD8+ T lymphocytes and macrophages to the tumor site and it is able to exert an anti-angiogenic effect. Similarly, a role of chemotactic attraction is exerted by TARC chemokine, which is responsible for the selective migration of activated Th2 effector cells toward the neoplastic tissues.

Together with the above mentioned cytokines, the PDMSC conditioned medium analysis, performed by Ray-Bio® Human Cytokine Antibody Array 5 kit, showed the presence of other functional modulators secreted by placental mesenchymal stem cells derived from a preeclamptic placenta, thus identifying a distinct protein expression profile.

Therefore, in an another embodiment, the conditioned medium which is the subject-matter of the invention, also comprises soluble fms-like tyrosine kinase-1 (sFlt-1), Interleukine-6 (IL-6), Interleukine-8 (IL-8) and/or tumor necrosis factor alpha (TNF-alpha). sFlt-1 is a soluble molecule with a powerful anti-angiogenic activity; IL-6, IL-8 and TNF-alpha are potent pro-inflammatory cytokines mediators of cytotoxicity against tumoral cells.

Preferably, the conditioned medium which is the subject-matter of the present invention comprises one or more proteins selected from the group consisting of ENA-78, GRO, GRO-alpha, IL-5, IL-7, IL-10, IL-15, IL-16, MCP-1, MCP-2, MCSF, MDC, ANGIOGENIN, ONCOSTATIN m, VEGF, BDNF, BLC, CKb 8-1, EOTAXIN 2, EOTAXIN 3, FLT-3 LIGAND, FRACTALKINE, GCP-2, GDNF, HGF, IFN-gamma, IGFBP-1, IGFBP-2, IGFBP-4, LIF, LIGHT, MCP-3, MCP-4, MIF, MIG, MIP-3alpha, MIP-1beta, MIP-16, NAP-2, NT-3, OSTEOPONTIN, OSTOPROTEGERIN, PDGFBB, RANTES, SCF, SDF, TGF-beta 1, TGF-beta 2, TGF-beta 3, TIMP-1 and TIMP-2, EGF, Thrombopoietin, LEPTIN, Eotaxin, FGF-4, FGF-6, FGF-7, FGF-9, IGFBP-3, NT-4, PARC, PIGF, and any combination thereof.

The cytokines analysis performed by the inventors did not find, in the conditioned medium which is the subject-matter of the present invention, the following proteins, because they were absent or present at very low concentrations and/or at concentrations lower than the detection limit of the array used: GM-CSF, 1-309, IL-1, IL-1b, IL-2, IL-3, IL-4, IL-12, p40p70, IL-13, MIP-1, TNF-beta, IGF-I, IGFBP-4, TGF-beta 3.

In a preferred embodiment, the conditioned medium is used for the therapeutic treatment of an epithelial tumor, more preferably a breast tumor. In the context of the present description, the term "epithelial" indicates the histological origin of the proliferating tumor cells site of the neoplastic transformation.

Due to the absence of immunogenicity that characterizes PDMSCs cells, the conditioned medium of the invention may optionally include a cellular fraction which consists of the preeclamptic placental mesenchymal stem cells from which it was obtained. Alternatively, the conditioned medium does not contain cellular fractions.

Within the scope of the present invention, there is also included a method to obtain the above described conditioned medium that includes the following steps:
(i) culturing a placental mesenchymal stem cell from a preeclamptic placenta in a serum-free liquid basal culture medium for at least three hours;
(ii) separating in whole or in part the cellular fraction from the liquid culture medium.

In the context of the present description the term "basal" is referred to a culture medium containing inorganic salts, amino acids and vitamins normally required to support the growth of mammalian cells that do not have special nutritional needs. By way of example and not limitation, the following liquid culture media, that differ essentially for salts and amino acids contents, are cited: Basal Medium Eagles (BME), Minimum Essential Medium (MEM), Dulbecco's Modified Eagle's Medium (DMEM), Nutrient Mixture F-10 (HAM's F-10) and Nutrient Mixture F-12 (HAM's F-12). The selection of the more appropriate culture medium is within the skills of the person skilled in the art.

According to the method of the invention, the culture medium is not supplemented by serum, in order to avoid that the growth factors contained in the serum will interfere and alter the effects caused by the specific factors secreted by PDMSC cells from preeclamptic placentae.

Before collecting the conditioned medium, placental mesenchymal stem cells from a preeclamptic placenta are cultured for a sufficient time to allow their adhesion to the culture substrate, their multiplication and the secretion of the components that characterize the above described medium and that make it beneficially effective for the therapeutic treatment of a tumor. This time period is at least of 3 hours, preferably at least 12 hours, at least 24 hours, at least 48 hours, at least 72 hours or at least 96 hours or at least 120 hours or at least 1 week or more.

In order to completely or partially separate the cellular fraction from the conditioned medium obtained from PDMSC cells from a preeclamptic placenta, it can be employed any method known per se. For example, the conditioned medium of the invention can be filtered using filtering complexes of adequate porosity to retain the cellular elements and their residues in suspension. Alternatively, the separation of conditioned medium from the PDMSC cells from which it was obtained, can be achieved by centrifugation and resulting sedimentation of the cells themselves. Therefore, in a preferred embodiment of the invention, the separation of the conditioned medium of the invention from the cellular components is performed by filtration or centrifugation or combination of both. The choice of the separation method is largely within the knowledge and technical skills of the person skilled in the art.

The scope of the present invention also includes a pharmaceutical composition comprising at least the proteins IP-10 and TARC, above identified as pivotal for the antitumoral activity of the conditioned medium subject of the present invention. Additional optional components of the pharmaceutical composition according to the invention are the following proteins: sFlt-1, TNF-alpha, ENA-78, GRO, GRO-alpha, IL-5, IL-7, IL-6, IL-8, IL-10, IL-15, IL-16, MCP-1, MCP-2, MCSF, MDC, ANGIOGENIN, ONCOSTATIN m, VEGF, BDNF, BLC, CKb 8-1, EOTAXIN 2, EOTAXIN 3, FLT-3 LIGAND, FRACTALKINE, GCP-2, GDNF, HGF, IFN-gamma, IGFBP-1, IGFBP-2, IGFBP-4, LIF, LIGHT, MCP-3, MCP-4, MIF, MIG, MIP-3alpha, MIP-1beta, MIP-16, NAP-2, NT-3, OSTEOPONTIN, OSTOPROTEGERIN, PDGFBB, RANTES, SCF, SDF, TGF-beta 1, TGF-beta 2, TGF-beta 3, TIMP-1 and TIMP-2, EGF, Thrombopoietin, LEPTIN, Eotaxin, FGF-4, FGF-6, FGF-7, FGF-9, IGFBP-3, NT-4, PARC, PIGF, and any combination thereof. In addition to the therapeutically active molecules, the pharmaceutical composition object of the invention includes suitable excipients, vehicles and/or pharmaceutically acceptable diluents which choice is within the skills of the average technician in the field.

Preferably, the pharmaceutical composition according to the invention is in a formulation suitable for systemic administration, more preferably by injection, in order to ensure its effective diffusion into the systemic blood flow. Of course, in the context of the present invention is included the use of injective systems of any type, the selection of which is within the skills of the person skilled in the art.

In an alternative embodiment, the pharmaceutical composition of the invention is in any pharmaceutical formulation suitable for oral administration, whose selection and preparation is within the skills of the person skilled in the art.

The following examples are provided to further illustrate and not to limit the scope of the invention as defined in the appended claims.

EXAMPLE 1: MESENCHYMAL STEM CELLS ISOLATION FROM A PREECLAMPTIC PLACENTA (PDMSCS)

Placenta-derived Mesenchymal Stem Cells (PDMSCs) were isolated from the basal plate of placentae derived from preeclamptic pregnancies.

Diagnosis of preeclampsia was made accordingly to the criteria established by the American College of Obstetricians and Gynecologists (ACOG): presence of pregnancy induced hypertension (systolic $\geq 140$ mmHg, dyastolic $\geq 90$ mmHg) and proteinuria ($\geq 300$ mg/24 h) after the 20 weeks of gestation in previously normotensive women. Pregnancies with congenital malformations, chromosomal anomalies (of number and/or structure) or evident intrauterine infections were excluded.

Collection of the placentae and subsequent placental tissue sampling were performed after delivery following patient informed consent and in accordance with the guidelines of the ethics committee of OIRM Sant'Anna-Mauriziano Hospital of Turin.

Membranes (amnion and chorion leave) were mechanically separated from the placental plate.

Full thickness tissue biopsies were excised from the placental basal plate (placental area formed by placental chorionic villi and in direct contact with the uterine wall) after mechanical removal of the decidua basalis (composed of maternal endometrial cells modified from the interaction with the syncytiotrophoblast).

Next, placental biopsies were washed several times at room temperature using sterile HBSS (Hank's Buffered Salt Solution, aqueous solution) (Gibco, Invitrogen by Life Technologies) in order to completely remove blood residues.

Biopsies were next mechanically homogenized and processed by enzymatic digestion using Collagenase I 100 U/ml (Gibco, Invitrogen by Life Technologies), 5 μg/ml Deoxyribonuclease I (DNAse I, Invitrogen by Life Technologies) dissolved in DMEM LG (Dulbecco's Modified Minimum Essential Medium Low Glucose without L-glutamin and without Fetal Bovine Serum-FBS), at 37° C. for 3 hours in a shacking thermostated water bath.

The resulting cell suspension was then centrifuged for 5 seconds, at 540 g at 4° C. in order to remove the undigested tissue residues. The supernatant was collected and filtered through Cells strainer filters with pores of 70 microns in diameter. After filtration, the solution was centrifuged for 5 minutes at 540 g, 4° C. in order to pellet the cells. The supernatant was then discarded and cells were re-suspended in sterile HBSS (30 ml for every 30 grams of the tissue of origin).

A volume of Ficoll Paque Premium 1,073 (GE Healthcare Europe) was layered under the cell solution obtained as described above, in the proportion of 1:3 relative to the starting volume. The preparation was centrifuged 20 minutes at 540 g, 20° C. and mononuclear cells ring, positioned in the gradient middle phase, was collected, resuspended in HBSS (50 ml for every 30 grams of original tissue) and centrifuged 10 minutes at 540 g, 20° C. in order to remove Ficoll residues.

After centrifugation, the supernatant was discarded and cells re-suspended in DMEM LG supplemented with 10% FBS (Gibco, Invitrogen by Life Technologies) and 0.1% Gentamicin. The cells were then plated in cell culture flasks and incubated at 37° C. and 5% CO2.

Cells were maintained in culture at 37° C., 5% CO2. At 90% of confluence, cells were splitted by treatment with trypsin TrypLE Express (trypsin of vegetable origin without animal derivates, GMP certified, Invitrogen Life Technologies) in order to promote cell expansion.

EXAMPLE 2: CHARACTERIZATION OF PDMSCS CELLS DERIVED FROM A PREECLAMPTIC PLACENTA

Mesenchymal stem cells isolated from placentae complicated by preeclampsia (chorionic portion of the basal plate) as described in the example 1, were characterized by cytofluorimetry by analyzing the main surface antigenic markers typical of this cell type.

The presence or absence of these antigens were evaluated by using monoclonal antibodies conjugated with fluorocromes (Myltenyi, Bologna, Italy). By fluorescence evaluation, it was demonstrated that all PDMSC cell lines from preeclamptic placentae were positive for the expression of surface markers CD105, CD166, CD90 and CD73 and negative for the expression of HLAII, CD34, CD133, CD20, CD326, CD31 and CD14, thus showing an appropriate mesenchymal phenotype and excluding any contamination from epithelial/trophoblast cells and haematopoietic progenitors. Moreover, the cell phenotype analysis was conducted by performing RT-PCR experiments that showed the expression by PDMSCs cells of Oct4 (Octamer-binding transcription factor 4) and NANOG (Homeobox protein NANOG) genes, typical of embryonic stem cells.

In order to evaluate PDMSCs stemness, at the third passage of culture cells were examined for their differentiation potential in three different lineage: osteoblasts, adipocytes and chondroblasts. Differentiation was obtained by using specific induction media. For osteogenic differentiation, cell cultures were incubated in α-MEM supplemented with 20% FCS, 100 U/ml penicillin, 100 μg/ml streptomycin, 2 mM L-glutamine, 20 mM phosphate-glycerol, 100 nM dexamethasone and 250 μM ascorbate-2-phosphate. For adipogenic differentiation, cell cultures were incubated with α-MEM supplemented with 20% FCS, 100 U/ml penicillin, 100 μg/ml streptomycin, 12 mM L-glutamine, 5 μg/ml insulin, 50 uM indomethacin, $1 \times 10^{-6}$ M dexamethasone and 0.5 uM 3-isobutyl-1-methylxanthine. For chondrogenic differentiation, the cultures were incubated in chondrocyte Basal Medium supplemented with R3-IGF-1 mL, bFGF 2.5 ML, 0.5 mL transferrin, bovine insulin 1 M, 25 mL FBS and gentamicin/amphotericin-B 0.5 mL. The medium was changed twice a week for three weeks. Cellular differentiation was assessed by using appropriate colorations. The osteoblast differentiation was assessed by staining with Alizarin Red S. Alizarin determines the formation of insoluble and intensely colored calcium plaques, thus allowing to highlight the bone matrix. Chondrogenic differentiation was assessed by Alcian Blue staining that form salt bridges between acid mucopolysaccharides polyanions and lets glycosaminoglycans being colored of blue. Adipogenic differentiation was evaluated by Oil Red staining, which highlights the lipids solubilized by the solvent present in the dye solution and the fat deposits are red-colored.

EXAMPLE 3: PRODUCTION OF THE CONDITIONED MEDIA

In order to obtain the conditioned medium which is the subject-matter of the invention, preeclamptic PDMSCs were plated between passages 3 to 5, when they reached the appropriate degree of purity, as demonstrated by the absence of trophoblastic and/or haematopoietic contaminant cells derived from the placental tissue of origin. Specifically, cells were plated at a density of $1 \times 10^5$ cells/ml in DMEM LG without Fetal Bovine Serum (FBS) at a temperature of 37° C. and 5% CO2. PDMSC were cultured for at least 3 hours to a week or more. Conditioned media were then collected at the established time points, subsequently centrifuged and/or filtered to remove contaminant cellular debris. When necessary, conditioned media obtained as just described could be preserved by freezing them at −80° C.

EXAMPLE 4: ANALYSIS OF THE CONDITIONED MEDIUM BY CYTOKINE ARRAY

The commercially available RayBio® Human Cytokine Antibody Array 5 kit, which enables simultaneous analysis of 80 different cytokines in the same sample, was used according to the manufacturer's instructions, to investigate the profile of cytokines which are secreted by preeclamptic PDMSC cells and which are present in the conditioned medium of the invention. Specifically, the procedure is based on antibodies spotted on an array membrane and able to recognize and capture the cytokines when present in the analyzed sample. In the context of this experiment, the signals generated on the array membrane at the sites of immune-complexes formation were quantified by densitometric analysis using the ImageQuant software. Expression levels of the identified cytokines were not determined as absolute values, but normalized as percentage compared to a group of standard controls included in the kit, assigning to the positive controls the value 100% and to the negative controls a value of 0%. The results of the above described experiment are shown in the following table:

| Protein | % relative to standards |
| --- | --- |
| ENA-78 | 38.1% |
| GRO | 79.4% |
| GRO-alfa | 11.1% |
| IL-6 | 105.8% |
| IL-7 | 6.4% |
| IL-8 | 128.9% |
| MCP-1 | 74.1% |
| MCP-2 | 8.7% |
| MCSF | 6.9% |
| MDC | 5.1% |
| ANGIOGENIN | 25.8% |
| ONCOSTATIN m | 8.5% |
| VEGF | 27.9% |
| BDNF | 19.8% |
| BLC | 10% |
| CKb 8-1 | 4.8% |
| EOTAXIN 2 | 2.5% |
| EOTAXIN 3 | 1.3% |
| FLT-3 LIGAND | 11.6% |
| FRACTALKINE | 12.4% |
| GCP-2 | 8.5% |
| GDNF | 8.3% |
| HGF | 2.1% |
| IGFBP-1 | 3.8% |
| IGFBP-2 | 14.5% |
| IGFBP-4 | 16.9% |
| IP-10 | 16.7% |
| LIF | 13.6% |
| LIGHT | 7.6% |
| MCP-4 | 23.3% |
| MIF | 11% |
| MIP-3alfa | 4.3% |
| NAP-2 | 16% |
| NT-3 | 20.2% |
| OSTEOPONTIN | 43.7% |
| OSTOPROTEGERIN | 35% |
| TGF-beta 2 | 29.9% |
| TIMP-1 | 33.4% |
| TIMP-2 | 71.4% |
| MIG | 7% |
| IL-5 | 2.7% |
| TGF-β3 | 8.7% |
| MIP-1beta | 13.7% |
| PDGFBB | 13.8% |
| SDF | 7.1% |
| IL-10 | 2.7% |
| IL-15 | 5.4% |
| IFN-gamma | 3.5% |
| MCP3 | 13.3% |
| MIP-16 | 1.5% |
| RANTES | 7.4% |
| SCF | 5.2% |
| TARC | 15.4% |
| TGF-beta1 | 6.8% |
| TNF-alfa | 11.1% |
| EGF | 4.7% |
| Thrombopoietin | 1.7% |
| LEPTIN | 14.9% |
| Eotaxin | 2.3% |
| FGF4 | 2.4% |
| FGF6 | 7% |
| FGF7 | 3.9% |
| FGF9 | 9.8% |
| IGFBP-3 | 3.4% |
| IL-16 | 5.4% |
| NT-4 | 2% |
| PARC | 9.8% |
| PlGF | 12.8% |

Moreover, cytokine analysis did not detected the presence of the following proteins in the conditioned medium object of the invention, because they were absent or below the detection limit of the array: GM-CSF, 1-309, IL-1a, IL-1b, IL-2, IL-3, IL-4, IL-12, p40p70, IL-13, MIP-1, TNF-beta, IGF-I, IGFBP-4, TGF-beta 3.

Anti-angiogenic sFlt-1, produced by preeclamptic mesenchymal stem cells, was detected by Real Time PCR (Polymerase Chain Reaction, to assess gene expression levels) and Western Blot analysis (to assess protein expression levels). Real Time PCR was performed on the mRNA (messenger RNA) isolated from the above mentioned placental cells derived from preeclamptic placentae using a specific custom set of primers and probe TaqMan produced by Life Technologies-Applied Biosystems Division following our request. These primers and probes were based on the sequences previously published by Nevo O. et al. J. Clin. Endocrinol. Metab. 2008 93:285-292. Western Blot analysis was performed by using a specific polyclonal antibody anti.sFlt-1 purchased from Life Technologies-Invitrogen (catalogue number 36-1100), following manufacturer instructions. Real Time PCR and Western Blot analyses showed a significantly increased production of sFlt-1 by preeclamptic placental mesenchymal stem cells relative to physiological controls at both gene (4.5 Fold Increase, $p<0.001$) and protein (2 Fold Increase, $p<0.05$) levels.

EXAMPLE 5: EVALUATION OF THE THERAPEUTIC EFFICACY OF CONDITIONED MEDIUM OBTAINED FROM CULTURED PDMSC CELLS FROM A PREECLAMPTIC PLACENTA

In order to evaluate the therapeutic efficacy of the conditioned medium object of the invention, specific studies have been conducted using in-vitro models represented by tumoral tissue explants excised from primary and metastatic tumors obtained from patients who underwent surgery for the removal of breast cancer and its metastases. In particular, it was verified whether the treatment of such explants with the conditioned medium of the invention induces a reduction of the expression levels of VEGF, JunB and PARP and an increase of the expression of Caspase 3 (CASP3) and p16INK4a, as an indication of a significant anti-angiogenic and anti-tumoral activity. Several clinical and experimental evidences demonstrated that VEGF is over-expressed in cancer and that it is an index of tumoral aggressiveness since it induces new vessels formation that bring nutrients to the tumoral tissue. JunB is an oncogene whose expression is directly associated with a bad prognosis of breast cancer. PARP (Poli-(ADP-ribose)-polymerase) is a nuclear protein that repairs DNA damages caused by chemotherapeutic agents, thus conferring to the tumoral tissue resistance to chemotherapy. CASP3 and p16Ink4A are two potent oncosuppressors able to induce apoptosis and block cell proliferation.

For the experimental procedures, tumoral tissue samples, excised from tissutal residues taken from three different patients after the routine post operative anatomo-pathological procedures, were used. From each tumor, eight explants were excised and cultured on Matrigel-filled inserts. Cultures were treated for 48 hours using the conditioned medium obtained by culturing preeclamptic PDSMCs for 48 hours as previously described.

In detail, the explants, consisting of a primary tumoral tissue (5 mm diameter) with conserved morphology and structure and of equal weight, were excised, plated on the insert containing 150 µl of Matrigel and maintained in 500 µl of HAM F12 medium without FBS for 12 hours at 37° C., 5% $CO_2$ in order to equilibrate their conditions after the post-operative stress. After 12 hours, the medium was exchanged with 500 µl of conditioned medium (12 explants) or with 500 µl of DMEM LG medium without serum (12 control explants). Cultures were incubated for further 48 hours under the same experimental conditions. At the end of the experiment, both treated and control explants were collected and processed for mRNA isolation using TRIzol reagent (Invitrogen Life Techonologies) following manufacturer instructions. Once isolated, mRNA was purified by DNAase (Sigma-Aldrich) treatment in order to remove genomic DNA contaminations. RNA concentration was determined by spectrophotometer reading at 260 nm wave length, while RNA purity was assessed by evaluating A260/A280 absorbance ratio at 1.8-2.

cDNA (complementary DNA), useful for the subsequent analysis performed to investigate VEGF, JunB, PARP, CASP3 and p16INK4a expression levels, was synthesized by RT-PCR from 5 micrograms of total RNA previously extracted using a random hexamers approach and the kit RevertAid H Minus First Strand cDNA Synthesis (Fermentas Life Science) according to manufacturer protocol.

VEGF, JunB, PARP, CASP3 and p16Ink4A gene expression analysis after treatment of tumoral cultures with the conditioned medium of the invention, was performed by Real Time PCR using TaqMan primers and probe (Life Technologies-Applied Biosystem Division). In order to perform a relative quantification, Real Time PCR signals were compared between the two groups of samples after normalization with the signals of the ribosomal 18S subunit, used as internal reference.

Figure 2:
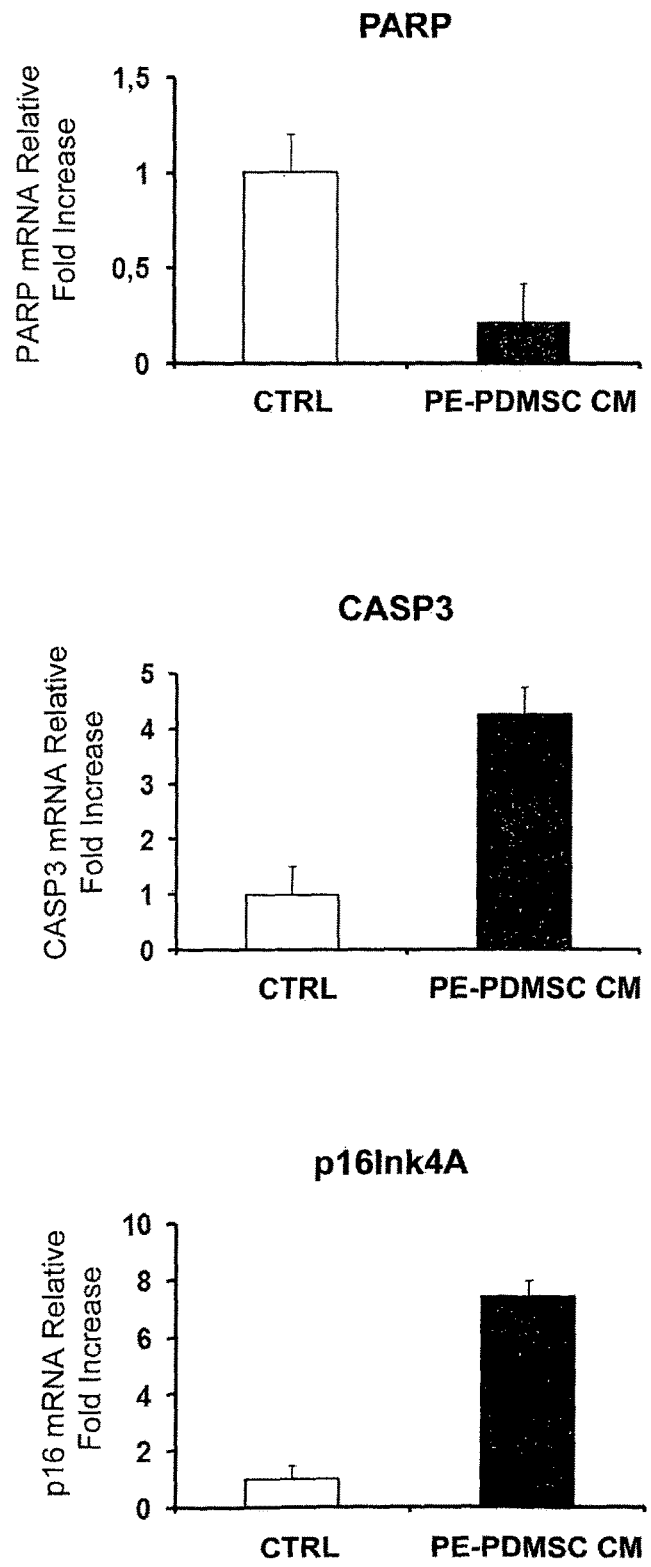
FIG. 2 shows treatment of primary and metastatic tumoral breast tissue explants by the disclosed conditioned media induces a decrease in PARP gene expression levels accompanied by an increase of CASP3 and p16Ink4A gene expression levels in the tumoral explants (p<0.05).

Differential gene expression results, represented by the histograms reported in FIG. 1 and FIG. 2, clearly demonstrated that the treatment with the conditioned medium (CM) object of the invention induced a statistically significant reduction of VEGF, JunB and PARP gene expression levels accompanied by an increase of CASP3 and p16Ink4A gene expression levels in the tumoral explants ($p<0.05$).

The invention claimed is:

1. A method of altering the expression of genes associated with cancer in a patient affected by cancer, comprising administering a conditioned medium to the patient, wherein the conditioned medium is obtainable by culturing placental mesenchymal stem cells from a preeclamptic placenta in a serum-free basal liquid culture medium, the conditioned medium comprising at least interferon gamma-induced protein 10 (IP-10) and thymus activation-regulated chemokine (TARC), and wherein the genes associated with cancer comprise VEGF, JunB, PARP, CASP3, p16nk4A, or any combination thereof.

2. The method according to claim 1, wherein the patient has an epithelial tumor.

3. The method according to claim 2, wherein the patient has a breast tumor.

4. The method according to claim 1, wherein the conditioned medium further comprises at least a protein selected from the group consisting of soluble fms-like tyrosine kinase-1 (sFlt-1), interleukin-6 (IL-6), interleukin-8 (IL-8) and tumor necrosis factor-alpha (TNF-alpha), or any combination thereof.

5. The method according to claim 1, wherein the conditioned medium further comprises one or more proteins selected from the group consisting of ENA-78, GRO, GRO-alpha, IL-5, IL-7, IL-10, IL-15, IL-16, MCP-1, MCP-2, MCSF, MDC, ANGIOGENIN, ONCOSTATIN m, VEGF, BDNF, BLC, CKb 8-1, EOTAXIN 2, EOTAXIN 3, FLT-3 LIGAND, FRACTALKINE, GCP-2, GDNF, HGF, IFN-gamma, IGFBP-1, IGFBP-2, IGFBP-4, LIF, LIGHT, MCP-3, MCP-4, MIF, MIG, MIP-3alpha, MIP-1beta, MIP-16, NAP-2, NT-3, OSTEOPONTIN, OSTOPROTEGERIN, PDGFBB, RANTES, SCF, SDF, TGF-beta 1, TGF-beta 2, TGF-beta 3, TIMP-1 and TIMP-2, EGF, Thrombopoietin, LEPTIN, Eotaxin, FGF-4, FGF-6, FGF-7, FGF-9, IGFBP-3, NT-4, PARC, PlGF, or any combination thereof.

6. The method according to claim 1, wherein the placental mesenchymal stem cells are of chorionic or amniotic origin.

7. The method according to claim 1, wherein the conditioned medium is cell free.

8. The method according to claim 1, wherein the placental mesenchymal stem cells from a preeclamptic placenta are of human origin.

* * * * *